(12) United States Patent
Qiu et al.

(10) Patent No.: US 6,511,678 B2
(45) Date of Patent: *Jan. 28, 2003

(54) CONTROLLED RELEASE FORMULATION OF DIVALPROEX SODIUM

(75) Inventors: Yihong Qiu, Gumee, IL (US); J. Daniel Bollinger, Libertyville, IL (US); Sandeep Dutta, Waukegan, IL (US); Howard S. Cheskin, Glencoe, IL (US); Kevin R. Engh, Kenosha, WI (US); Richard P. Poska, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 4 days.

This patent is subject to a terminal disclaimer.

(21) Appl. No.: 09/748,567

(22) Filed: Dec. 22, 2000

(65) Prior Publication Data

US 2001/0020039 A1 Sep. 6, 2001

Related U.S. Application Data

(63) Continuation-in-part of application No. 09/216,650, filed on Dec. 18, 1998.

(51) Int. Cl.[7] ................................................. A61K 9/00
(52) U.S. Cl. ...................... 424/464; 442/465; 442/489; 442/499; 442/468; 442/470
(58) Field of Search ................................ 424/454, 486, 424/458, 459, 461, 462, 470, 490, 494, 495, 497

(56) References Cited

U.S. PATENT DOCUMENTS

| | | |
|---|---|---|
| 4,369,172 A | 1/1983 | Schor et al. |
| 4,699,927 A | 10/1987 | Deboeck |
| 4,913,906 A | 4/1990 | Friedman et al. |
| 4,988,731 A | 1/1991 | Meade |
| 5,009,897 A | 4/1991 | Brinker et al. |
| 5,017,613 A | 5/1991 | Aubert et al. |

(List continued on next page.)

FOREIGN PATENT DOCUMENTS

| | | |
|---|---|---|
| EP | 0 141 267 B1 | 8/1987 |
| EP | 0 430 287 B2 | 6/1991 |
| EP | WO 98/47491 | * 10/1998 |
| WO | WO 94/27587 | 12/1994 |
| WO | WO 00/37055 | 6/2000 |
| WO | WO 00/45793 A1 | 8/2000 |

OTHER PUBLICATIONS

Colins et al., "Depakote CR; Biopharmaceutical and Pharmacokinetic Studies of a New Formulation for Once Daily Dosing", Neurology, vol. 50(4), Supplemental 4, Apr. 1998, p. A426.*

(List continued on next page.)

Primary Examiner—Thurman K. Page
Assistant Examiner—Isis Ghali
(74) Attorney, Agent, or Firm—Paul D. Yasger

(57) ABSTRACT

A new oral polymeric controlled release formulation suitable for the once-a-day administration of valproate compounds, such as divalproex sodium, has been discovered. This formulation exhibits significant advantages over the sustained release valproate formulations of the prior art. This formulation minimizes the variation between peak and trough plasma levels of valproate over a 24 hour dosing period. This formulation follows a zero-order release pattern thus producing essentially flat plasma levels of valproate, once steady-state levels have been achieved. This results in a significantly lower incidence of side effects for patients consuming such a formulation.

8 Claims, 4 Drawing Sheets

U.S. PATENT DOCUMENTS

| | | | |
|---|---|---|---|
| 5,019,398 A | | 5/1991 | Daste |
| 5,055,306 A | | 10/1991 | Barry et al. |
| 5,169,642 A | | 12/1992 | Brinker et al. |
| 5,185,159 A | | 2/1993 | Aubert et al. |
| 5,212,326 A | | 5/1993 | Meade |
| 5,589,191 A | | 12/1996 | Ukigaya et al. |
| 5,593,690 A | * | 1/1997 | Akiyama et al. ............ 424/457 |
| 5,593,694 A | * | 1/1997 | Hayashida et al. ......... 424/464 |
| 6,077,542 A | | 6/2000 | Sherman |
| 6,150,410 A | | 11/2000 | Engh et al. |

OTHER PUBLICATIONS

Colins, et al., "Depakote CR: Biopharmaceutical and Pharmacokinetic Studies of a New Formulation for Once Daily Dosing", Neurology, vol. 50(4), Supplement 4, Apr. 1998, p. A426.

Samara, et al., "Bioavailability of a ControlledRelease Formulation of Depakote", No. 3.053, Epilepsia, vol. 38, Suppl. 8, 1997.

Cavanaugh, et al., "Effect of Food on the Bioavailability of a ControlledRelease Formulation of Depakote Under MultipleDose Conditions", No. 2.002, Epilepsia, vol. 38, Suppl. 8, 1997.

Freitag, et al., "Depakote ER in Migraine Prophylaxis", Abstract No. S07.003, Nuerology 54 Apr. 2000 (Suppl 3), p. A14.

*Physicians' Desk Reference*, (Web Version), 2001, Depakote ER, published by The Medical Economics Company.

Abstract of Collins, et al., "Extended Release Formulations of Anticonvulsant Medications Clinical Pharmacokinetics and Therapeutic Advantages", CNS Drugs, New Zealand, 2000, 14/3 (203–212).

Abstract of Bialer, et al., "Criteria to Assess in Vivo Performance and Bioequivalence of Generic Controlled–Release Formulations of Carbamazepine", Epilepsia United States, 1998, 39/5 (513–519).

Abstract of Chun, et al., "Multiple–dose Evaluation of the Absorption Characteristics of Divalproex Sodium Tablets, a Delayed–Release Preparation of Valproate, in Healthy Volunteers", Clinical Drug Investigation, New Zealand, 1995, 10/1 (40–47).

Abstract of Bressolle, et al., "A Double Weibull Input Function Describes the Complex Absorption of Sustained–Release Oral Sodium Valproate", Journal of Pharmaceutical Sciences, United States, 1994, 83/10 (1461–1464).

Abstract of Hussein, et al., "Pharmacokinetics of Valproate after Multiple–dose Oral and Intravenous Infusion Administraton: Gastrointestinal–related Diurnal Variation", Journal of Clinical Pharmacology, United States, 1994, 34/7 (754–759.

Abstract of Wilder, et al., "Gastrointestinal Tolerance of Divalproex Sodium", Neurology, United States, 1983, 33/6 (808–811).

Abstract of Wilder, et al., "Twice–daily Dosing of Valproate with Divalproex", Clinical Pharmacology and Therapeutics, United States, 1983, 34/4 (501–504).

Bialer et al., Int. J. Pharmaceutics, 20: 53–63 (1984).

Bialer et al., Biopharmaceutics and Drug Dispositon, 6: 401–411 (1985).

Bialer et al., Israel J. Med. Sci., 20: 46–49 (1984).

Collins et al., Extended Release Formulations of Anticonvulsant Medications Clinical Pharmacokinetics and Therapeutic Advantages, CNS Drugs 200s0 Sep. 14 (3): 203–212.

* cited by examiner

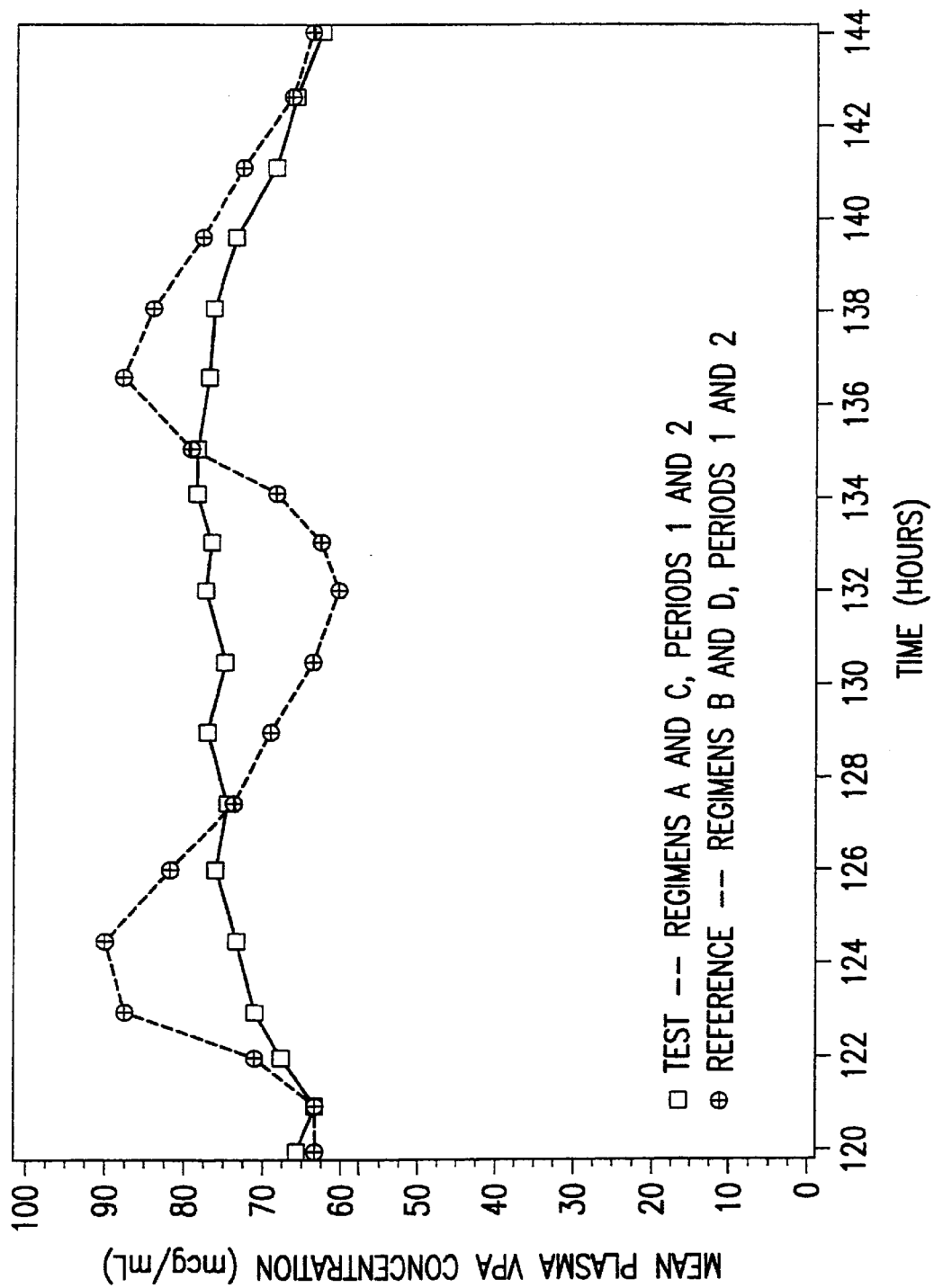

CONTROLLED RELEASE FORMULATION OF DIVALPROEX SODIUM

CROSS REFERENCE

This application is a continuation-in-part of U.S. patent application Ser. No. 09/216,650, filed Dec. 18, 1998, the contents of which are hereby incorporated by reference.

TECHNICAL FIELD

The present invention relates to pharmaceutical formulations. More particularly, the present invention concerns a formulation comprising valproic acid, a pharmaceutically acceptable salt, ester, or amide thereof, or divalproex sodium, in a controlled release formulation. These controlled release dosage forms have an improved pharmacokinetic profile. These dosage forms minimize the variance between peak and trough plasma levels of valproate, resulting in a reduction in the incidence of side effects.

BACKGROUND

2-Propylpentanoic acid, more commonly known as valproic acid ("VPA") is effective as an antiepilpetic agent. After ingestion, the free acid dissociates to the valproate ion within the gastrointestinal tract. The valproate ion is absorbed and produces the therapeutic effect described above. Physicians Desk Reference ("PDR"), 52$^{nd}$ Edition, page 426 (2000).

Divalproex sodium is effective in the treatment of epilepsy, migraine, and bipolar disorders. It also dissociates to the valproate ion within the gastrointestinal tract. This substance is described in more detail in U.S. Pat. No. 4,988,731, and U.S. Pat. No. 5,212,326, the contents of both, which are hereby incorporated by reference.

The acid moiety of valproic acid has been functionalized in order to produce prodrugs capable of generating a valproate ion in-vivo. For example, the amide of valproic acid, valpromide ("VPO"), has been produced, as well certain salts and esters of the acid.

Despite the efficacy of these drugs in the treatment of conditions such as epilepsy, they all suffer from a common disadvantage. These valproate compounds have a relatively short half life. For example, the half life of valproic acid is reported to be between six and seventeen hours in adults and between four and fourteen hours in children. This leads to substantial fluctuations in the plasma concentration of the drug, especially in chronic administration. To maintain reasonably stable plasma concentrations, it is necessary to resort to frequent dosing, and the resulting inconvenience to the patient often results in lowered compliance with the prescribed dosing regimen. Moreover, widely fluctuating plasma concentrations of the drug may result in administration of less than therapeutic amounts of the drug in a conservative dosing regimen, or amounts too large for the particular patient in an aggressive dosing regimen. The logical solution to this problem would be to develop sustained release dosage forms that decrease the dosing frequency of the compounds.

However, the pharmacokinetics of valproic acid, and other valproate compounds, has complicated such development efforts. The relationship between plasma concentration and clinical response is not well documented for valproate. One contributing factor is the nonlinear, concentration dependent protein binding of valproate, which affects the clearance of the drug. As the dose of valproate increases, serum levels rise faster than might be expected since proportionately less of the dose is bound to plasma proteins. For example, because the plasma protein binding of valproate is concentration dependant, the free fraction increases from approximately 10% at 40 $\mu$g/ml to 18.5% at 130 $\mu$g/ml.

These nonlinear kinetics significantly increase the difficulty of designing sustained release dosage forms. Identical doses of the valproate compound can produce vastly different blood levels depending upon the rate at which the valproate compound is released from the dosage form.

Further complicating development efforts is the fact that a correlation between valproate levels and efficacy is unknown for disease states other than epilepsy. For example, therapeutic concentrations required to treat migraine headaches and bipolar disorders have not been established.

What impact valproate levels play in a number of side effects is also unknown at the present time. GI irritation is very common in patients consuming valproate, affecting up to one third of patients. The incidence increases at elevated doses. It is unknown if this side effect is caused by local irritation within the GI tract or is mediated via the stimulation of a receptor within the central nervous system (and thus is dependant upon plasma valproate levels). Other side effects such as asthenia, dizziness, somnolence, alopecia, and weight gain are quite common. It is also unknown if these side effects can be correlated with plasma levels of valproate. A more detailed discussion of valproate side effects may be found in PDR supra, page 421–437.

In spite of the nonlinear kinetics of the compounds, a concerted effort has been devoted to the discovery of valproate formulations that will maintain more constant plasma levels of the drug following administration. The ultimate goal of these studies has been the discovery of a formulation which affords stable plasma levels in a once-a-day dosing regimen. These efforts fall generally into one of two categories: (a) finding a form of the active ingredient which is more slowly released to the body metabolically, and (b) finding a formulation which delivers the drug by either a timed- or controlled-release mechanism.

U.S. Pat. No. 4,369,172 to Schor, et al. describes, for example, a prolonged release therapeutic composition based on mixtures of hydroxypropyl methylcellulose, ethyl cellulose and/or sodium carboxymethyl cellulose. The patentees provide a long list of therapeutic agents which they suggest can be incorporated into the formulation including sodium valproate.

U.S. Pat. No. 4,913,906 to Friedman, et al. discloses a controlled release dosage form of valproic acid, its amide, or one of its salts or esters in combination with a natural or synthetic polymer, pressed into a tablet under high pressure.

U.S. Pat. No. 5,009,897 to Brinker, et al. discloses granules, suitable for pressing into tablets, the granules comprising a core of divalproex sodium and a coating of a mixture of a polymer and microcrystalline cellulose.

U.S. Pat. No. 5,019,398 to Daste discloses a sustained-release tablet of divalproex sodium in a matrix of hydroxypropyl methylcellulose and hydrated silica.

U.S. Pat. No. 5,055,306 to Barry, et al. discloses an effervescent or water-dispersible granular sustained release formulation suitable for use with a variety of therapeutic agents. The granules comprise a core comprising the active ingredient and at least one excipient, and a water insoluble, water-swellable coating comprising a copolymer of ethyl acrylate and methyl methacrylate and a water soluble hydroxylated cellulose derivative. The patentees suggest a list of therapeutic agents which may be used in the formulation of the invention, including sodium valproate.

U.S. Pat. No. 5,169,642 to Brinkler, et al. discloses a sustained release dosage form comprising granules of divalproex sodium or amides or esters of valproic acid coated with a sustained release composition comprising ethyl cellulose or a methacrylic methyl ester, a plasticizer, a detackifying agent, and a slow-release polymeric viscosity agent.

U.S. Pat. No. 5,185,159 to Aubert, et al. discloses a formulation of valproic acid and sodium valproate which is prepared without the use of either a binder or a granulating solvent. The formulation optionally contains precipitated silica as an anti-sticking or detackifying agent.

U.S. Pat. No. 5,589,191 to Exigua, et al. discloses a slow release sodium valproate tablet formulation in which the tablets are coated with ethyl cellulose containing silicic acid anhydride.

Published PCT application WO 94/27587 to Ayer, et al. discloses a method for control of epilepsy by delivering a therapeutic composition of divalproex sodium in combination with a poly (alkylene oxide).

Bialer, et al., "Metabolism of Antiepileptic Drugs," pp. 143–151, R. H. Levy, Ed., Raven Press, New York, 1984; *Int. J. Pharmaceutics*, 20: 53–63 (1984); and *Biopharmaceutics and Drug Disposition*, 6: 401–411 (1985); and *Israel J. Med. Sci.*, 20: 46–49 (1995) report the pharmacokinetic evaluation of several sustained release formulations of valproic acid.

Despite all of these efforts, there remains the need for a sustained release formulation of divaproex sodium, and other valproate compounds, that will permit once-a-day dosing. Further, there remains the need for a formulation which will effectively maintain plasma concentrations of the drug at more constant levels over a 24 hour dosing period (i.e. minimize the variation between peak and trough plasma levels). Further, sustained release formulations are needed that will decrease the incidence of side effects associated with valproate therapy. More specifically, there remains the need to reduce the incidence of nausea, vomiting, asthenia, somnolence, alopecia, weight gain, etc. in patients undergoing valproate therapy.

BRIEF DESCRIPTION OF THE DRAWINGS

In the drawings, which form a part of this specification:

FIG. 4 is a graphical representation of plasma valproate levels of a qd (once-a-day) and bid (twice-a-day) dosage form.

SUMMARY OF THE INVENTION

Figure 1:
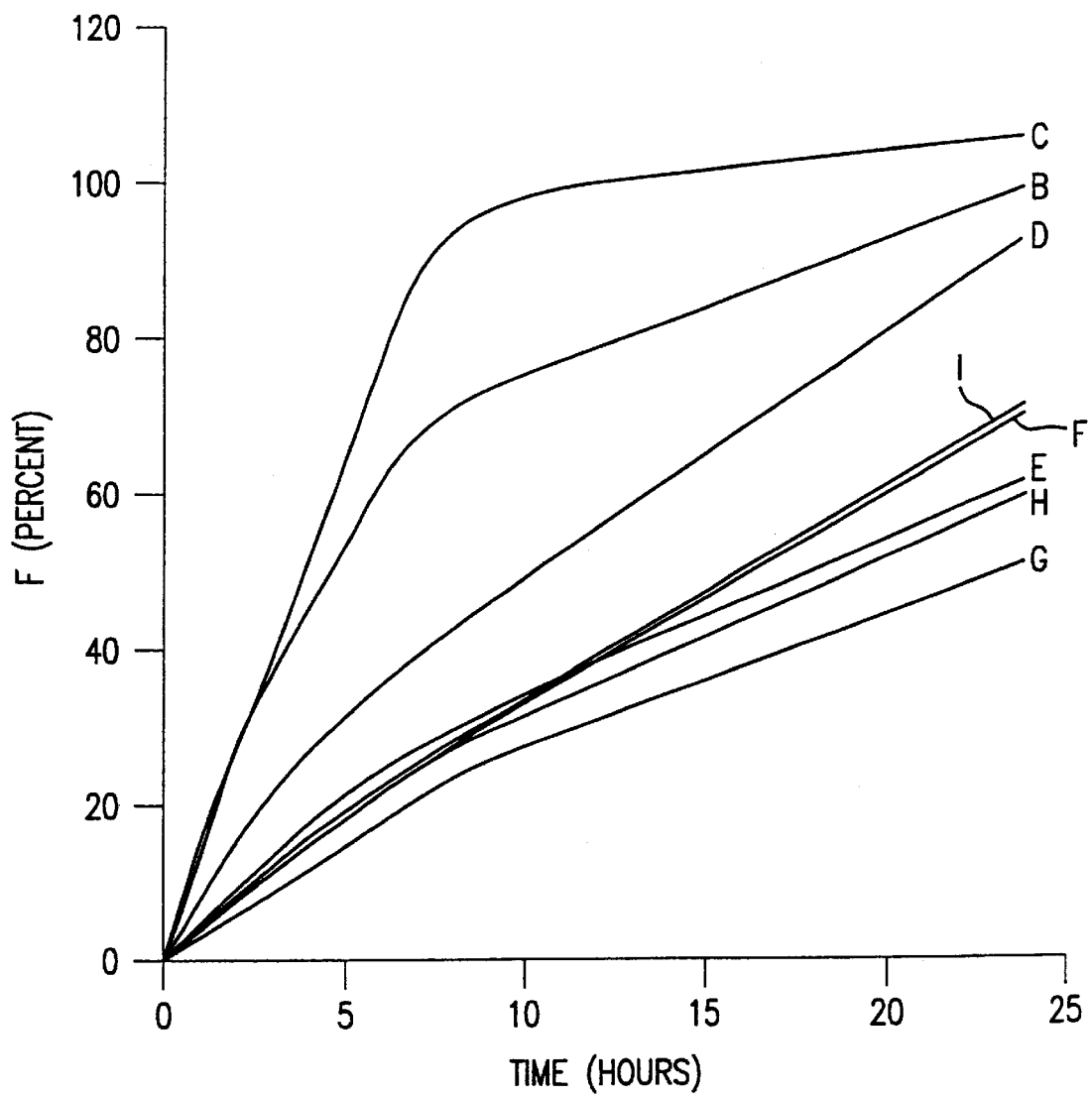
FIG. 1 is a graphical representation of the release of drug from several tests controlled release tablet formulations under in vitro conditions.

In accordance with the present invention, a new oral controlled release formulation suitable for the once-a-day administration of valproate compounds, such as divalproex sodium, has been discovered. This formulation exhibits significant advantages over the sustained release valproate formulations of the prior art. This formulation minimizes the variation between peak and trough plasma levels of valproate over a 24 hour dosing period. This formulation follows a zero-order release pattern thus producing essentially flat plasma levels of valproate, once steady-state levels have been achieved. This results in a significantly lower incidence of side effects for patients consuming such a formulation.

The qd formulation produces the following pharmacokinetic profile. Peak concentrations of valproate, $C_{max}$, are statistically significantly ($p<0.05$) below those produced by valproate dosage forms suitable for twice a day administration (over a 24 hour period). Trough levels of valproate, $C_{min}$, are not statistically significantly different from those obtained with a twice-a-day dosage form (over a 24 hour period). The extent of absorption, as defined by area under the curve (AUC), is equivalent to those produced by the twice a day valproate dosage forms (over a 24 hour period). Such a combination of properties has unexpected benefits. It allows therapeutic levels of valproate to be maintained over a 24 hour dosing period. Further, it has been discovered that a significantly lower incidence of side effects has been achieved by this reduction in peak plasma concentration. Gastrointestinal side effects, alopecia, and certain CNS side effects have been reduced.

The controlled release once-a-day formulation ("qd") is a hydrophilic matrix dosage form. It comprises a valproate compound that is in admixture with a sufficient quantity of at least one pharmaceutically acceptable polymer. A sufficient quantity of the polymer is utilized, so that said formulation exhibits the following in-vitro dissolution profile, when measured in a type 2 dissolution apparatus (paddle) at 100 rpm, at a temperature of 37±0.5° C., in 500 ml of 0.1N HCl for 45 minutes, followed by 900 ml of 0.05M phosphate buffer containing 75 mM sodium laurel sulfate (pH 5.5), for the remainder of the testing period:

i. no more than about 30% of total valproate is released after 3 hours of measurement in said apparatus;

ii. from about 40 to about 70% of total valproate is released after 9 hours of measurement in said apparatus;

iii. from about 55 to 95% of total valproate is released after 12 hour of measurement in said apparatus; and iv. not less than 85% of total valproate is released after 18 hours of measurement in said apparatus.

Upon ingestion, a formulation meeting this profile produces the $C_{max}$, $C_{min}$, and AUC described above. Further, this formula produces steady state plasma valproate levels having a degree of fluctuation that is lower than that produced by a corresponding twice-a-day valproate dosage form. The qd formulation also provides for total absorption of the valproate compound that is at least 80% of that achieved by a daily dose of the corresponding twice-a-day formulation. Such a pharmacokinetic profile leads to a reduction in side effects associated with valproate therapy.

A more specific embodiment of this invention is directed to a once-a-day divalproex sodium dosage form. This formulation will meet the dissolution profile listed immediately above. It has a degree of fluctuation that is less than that achieved by a divalproex sodium delayed release tablet. This qd dosage form also produces total valproate absorption that is at least 80% of that achieved by the divalproex sodium delayed release tablets. Peak steady state plasma valproate levels obtained with the qd dosage form are 10–20% lower than that produced by the divalproex sodium delayed release tablets. Trough levels, which are important in maintaining control of epileptic seizures, are not statistically significantly different from those obtained with the divalproex sodium delayed release tablets. This qd dosage form has a reduced incidence of side effects when compared to the divalproex delayed release tablets.

DETAILED DESCRIPTION
I. Definitions and Background Information

As noted above, the invention relates to new and improved dosage forms of valproic acid and other valproate compounds which disassociate in-vivo to produce a valproate ion. Several valproate compounds are currently available commercially in the United States or have been described in the literature.

One such compound is valproic acid. Valproic acid may be represented by the following structure:

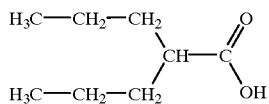

Valproic acid is available commercially from Abbott Laboratories of Abbott Park, Ill. Methods for its synthesis are described in Oberreit, Ber. 29, 1998 (1896) and Keil, Z. Physiol. Chem. 282, 137 (1947). It's activity as an antiepileptic compound is described in the Physician Desk Reference, $52^{nd}$ Edition, page 421 (1998). Upon oral ingestion within the gastrointestinal tract, the acid moiety disassociates to form a carboxylate moiety (i.e. a valproate ion).

The sodium salt of valproic acid is also known in the art as an anti-epileptic agent. It is also known as sodium valproate and is described in detail in The Merck Index, $12^{th}$ Edition, page 1691 (1996). Further descriptions may be found in the Physician Desk Reference, $52^{nd}$ Edition, page 417 (1998).

Divalproex sodium is effective as an antiepileptic agent and is also used for, migraine and bipolar disorders. Methods for its preparation may be found in U.S. Pat. Nos. 4,988,731 and 5,212,326, the contents of both which are hereby incorporated by reference. Like valproic acid, it also disassociates within the gastrointestinal tract to form a valproate ion.

In addition to these specific compounds, one of ordinary skill in the art would readily recognize that the carboxylic moiety of the valproate compound may be functionalized in a variety of ways. This includes forming compounds which readily metabolize in-vivo to produce valproate, such as valproate amide (valproimide), as well as other pharmaceutically acceptable amides and esters of the acid (i.e. prodrugs). This also includes forming a variety of pharmaceutically acceptable salts.

Suitable pharmaceutically acceptable basic addition salts include, but are not limited to cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Other possible compounds include pharmaceutically acceptable amides and esters. "Pharmaceutically acceptable ester" refers to those esters which retain, upon hydrolysis of the ester bond, the biological effectiveness and properties of the carboxylic acid and are not biologically or otherwise undesirable. For a description of pharmaceutically acceptable esters as prodrugs, see Bundgaard, E., ed., (1985) Design of Prodrugs, Elsevier Science Publishers, Amsterdam, which is hereby incorporated by reference. These esters are typically formed from the corresponding carboxylic acid and an alcohol. Generally, ester formation can be accomplished via conventional synthetic techniques. (See, e.g., March Advanced Organic Chemistry, $3^{rd}$ Ed., John Wiley & Sons, New York p. 1157 (1985) and references cited therein, and Mark et al. Encyclopedia of Chemical Technology, John Wiley & Sons, New York (1980), both of which are hereby incorporated by reference. The alcohol component of the ester will generally comprise (i) a $C_2$–$C_{12}$ aliphatic alcohol that can or can not contain one or more double bonds and can or can not contain branched carbons or (ii) a $C_7$–$C_{12}$ aromatic or heteroaromatic alcohols. This invention also contemplates the use of those compositions which are both esters as described herein and at the same time are the pharmaceutically acceptable salts thereof.

"Pharmaceutically acceptable amide" refers to those amides which retain, upon hydrolysis of the amide bond, the biological effectiveness and properties of the carboxylic acid and are not biologically or otherwise undesirable. For a description of pharmaceutically acceptable amides as prodrugs, see Bundgaard, H., Ed., (1985) Design of Prodrugs, Elsevier Science Publishers, Amsterdam. These amides are typically formed from the corresponding carboxylic acid and an amine. Generally, amide formation can be accomplished via conventional synthetic techniques. (See, e.g., March Advanced Organic Chemistry, $3^{rd}$ Ed., John Wiley & Sons, New York, p. 1152 (1985) and Mark et al. Encyclopedia of Chemical Technology, John Wiley & Sons, New York (1980), both of which are hereby incorporated by reference. This invention also contemplates the use of those compositions which are amides, as described herein, and at the same time are the pharmaceutically acceptable salts thereof. As used in this application:

a) any reference to "valproate" or "valproate compounds" should be construed as including a compound which disassociates within the gastrointestinal tract, or within in-vitro dissolution media, to produce a valproate ion including, but not limited to, valproic acid, the sodium salt of valproate, divalproex sodium, any of the various salts of valproic acid described above, and any of the prodrugs of valproic acid described above. Divalproex sodium is the most preferred valproate compound of the present invention.

b) "$C_{max}$" means maximum plasma concentration of the valproate ion, produced by the ingestion of the composition of the invention or the twice-a-day comparator (BID).

c) "$C_{min}$" means minimum plasma concentration of the valproate ion, produced by the ingestion of the composition of the invention or the BID comparator.

d) "$C_{avg}$" means the average concentration of valproate ion within the 24-hour interval produced by the ingestion of the composition of the invention or the BID comparator. $C_{avg}$ is calculated as AUC over a 24 hour interval divided by 24.s e) "$T_{max}$ means time to the maximum observed plasma concentration produced by the ingestion of the composition of the invention or the BID comparator.

f) "AUC" as used herein, means area under the plasma concentration-time curve, as calculated by the trapezoidal rule over the complete 24-hour interval for all the formulations.

g) "Degree of Fluctuation (DFL)" as used herein, is expressed as:
DFL=$(C_{max}-C_{min})/C_{avg}$ produced by the ingestion of the composition of the invention or the BID comparator.

h) "Pharmaceutically acceptable" as used herein, means those salts, polymers, and excipients which are, within the scope of sound medical judgment, suitable for use in contact with the tissues of humans and lower animals without undue toxicity, irritation, allergic response, and the like, in keeping with a reasonable benefit/risk ratio, and effective for their intended use in the treatment and prophylaxis of migraine, epilepsy, bipolar disorders, etc.

i) "Side effects" as used herein, means those physiological effects to various systems in the body such as cardiovascular, nervous, digestive, and the body as a whole, which cause pain and discomfort to the individual subject, and which are the direct result of the ingestion of the valproate compound.

j) "Decreased incidence of side effects" refers to a reduced incidence of side effects in a patient population, and not to a total absence of side effects, when measured in a comparable population consuming a valproate dosage form suitable for twice daily administration. As is well known to those skilled in the art, even placebo dosage forms made of sugar produce some measurable incidence of side effects. Thus an improved side effect profile must be interpreted in light of the relevant art.

k) "delayed release divalproex sodium tablets" refers to an enteric coated dosage form containing divalproex sodium intended to delay the release of the medication until the dosage form has passed through the stomach.

l) "bid" refers to the administration of a formulation twice during a 24 hour period.

m) "qd" refers to the administration of a formulation once during a 24 hour period.

n) Any reference in the specification, or claims, to an in-vitro dissolution profile should be construed as referring to a dissolution test in which the total amount of valproate released is measured utilizing a Type 2 apparatus (paddle) at 100 rpm, a temperature of 37±0.5 C., a test solution of 500 ml of 0.1N HCl for the first 45 minutes, followed by a test solution of 900 ml of 0.05M phosphate buffer containing 75 mM sodium laurel sulfate (pH5.5) for the remainder of the testing period, and utilizing one tablet (i.e. a single dosage form).

o) A statistical test is said to be "statistically significant" when the resulting p-value is less than or equal to 0.05, unless otherwise noted. "Equivalence" and "statistical significance" are not synonyms.

As used in this application, the terms "$C_{min}$" and "trough levels", should be considered synonyms. Likewise, the terms "$C_{max}$" and "peak levels" should also be considered synonyms. Any reference to a plasma concentration of valproate ion, and more specifically to any quantification thereof, such as, for example, $C_{min}$, $C_{max}$, AUC, DFL, etc., should be considered to have been determined at steady state in a fasting population, unless expressly stated otherwise.

As is well known to those skilled in the art, in-vitro dissolution profiles are routinely used in the manufacture of pharmaceuticals. They serve as quality control devices to insure that different batches will have the same dissolution profile and thus produce comparable biological responses. Sometimes, dissolution profiles can serve as a reliable predictor of in-vivo blood levels. This is accomplished by establishing an in-vivo/in-vitro correlation (iv/ivc). Methods for carrying out such studies are described by the FDA at www.usfda.gov. The procedure outlined by the FDA in this website was utilized in developing the dissolution profiles described above and throughout this application.

Thus, the in-vitro dissolution profile described above is a reliable predictor of the pharmacokinetic profile of a hydrophilic matrix dosage form. Any valproate containing hydrophilic matrix formulation meeting the dissolution parameters above will provide the advantages of once daily dosing and a decreased incidence of side effects. Such benefits will be obtained regardless of the specific polymers or excipients contained within the hydrophilic matrix formulation.

The dissolution testing described above is carried out as is known in the art. A detailed discussion of such techniques may be found in United States Pharmacopeia (USP) Vol. 23, pp. 1791–1793 (1995). It is important to note that all of the compounds encompassed by this invention disassociate within the gastrointestinal tract to generate a valproate ion, which is ultimately responsible for the biological activity. Therefore, even though a compound such as divalproex sodium is introduced into the dissolution media, the media is assayed for valproate content, not divalproex content, etc. Methods for assaying valproate content may be accomplished using a TDX fluoresence radioimmune assay which is available from Abbott Laboratories. Methods for carrying out this assay are described in the TDX system operation manual, List No. 9520-22 Abbott Laboratories, Diagnostics Division, Abbott Park, Ill. 60064 (1992).

II. Dosage Forms

As noted above, a new valproate dosage form has been discovered that possess significant advantages over the sustained release formulations of the prior art. These formulations provide zero (0) order release of valproate, minimizing the variance between peak and trough plasma levels of valproate. All of the formulations of this invention are matrix systems.

Matrix systems are well known in the art. In a matrix system, the drug is homogenously dispersed in a polymer in association with conventional excipients. This admixture is typically compressed under pressure to produce a tablet. Drug is released from this tablet by diffusion and erosion. Matrix systems are described in detail by (i) Handbook of pharmaceutical controlled release technology, Ed. D. L. Wise, Marcel Dekker, Inc. New York, N.Y. (2000), and (ii) Treatise on controlled drug delivery, fundamentals, optimization, applications, Ed. A. Kydonieus, Marcel Dekker, Inc. New York, N.Y. (1992), both of which are hereby incorporated by reference.

The enhanced pharmacokinetic profile, described in detail below, can be obtained by the administration of a hydrophilic matrix formulation suitable for once-a-day administration comprising:

a) a valproate compound, typically present in an amount sufficient to provide the required daily dose of said valproate compound, and;

b) said valproate compound is in admixture with a sufficient quantity of a pharmaceutically acceptable polymer, so that said formulation exhibits the following in-vitro dissolution profile, when measured in a type 2 dissolution apparatus (paddle) at 100 rpm, at a temperature of 37±0.5 C., in 500 ml of 0.1N HCl for 45 minutes, followed by 900 ml of 0.05M phosphate buffer, containing 75 mM sodium laurel sulfate (pH 5.5), for the remainder of the testing period:

i. no more than about 30% of total valproate is released after 3 hours of measurement in said apparatus;

ii. from about 40 to about 70% of total valproate is released after 9 hours of measurement in said apparatus;

iii. from about 55% to about 95% of total valproate is released after 12 hour of measurement in said apparatus, and;

iv. not less than 85% of total valproate is released after 18 hours of measurement in said apparatus.

In a more preferred embodiment, the formulation exhibits the following in-vitro dissolution profile, when tested under the same conditions:

a. from about 15% to about 30% of total valproate is released after 3 hours of measurement in said apparatus;
b. from about 40% to about 70% of total valproate is released after 9 hours of measurement in said apparatus;
c. from about 55% to about 90% of total valproate is released after 12 hours of measurement in said apparatus, and;
d. not less than 88% of total valproate is released after 18 hours of measurement in said apparatus.

In a more specific embodiment, the formulation exhibits the following in-vitro dissolution profile, when tested under the same conditions:

i. from about 15% to about 27% of total valproate is released after 3 hours of measurement in said apparatus;
ii. from about 44% to about 69% of total valproate is released after 9 hours of measurement in said apparatus;
iii. from about 59% to about 90% of total valproate is released after 12 hours of measurement in said apparatus, and;
iv. not less than 88% of total valproate is released after 18 hours of measurement in said apparatus.

The matrix formulations of this invention comprise a valproate compound and a pharmaceutically acceptable polymer. Preferably, the valproate compound is divalproex sodium. The amount of the valproate compound varies from about 40% to about 80% by weight of the dosage form. Preferably, the dosage form comprises about 45% to about 65% by weight of the valproate compound.

The pharmaceutically acceptable polymer is a water-soluble hydrophilic polymer, or a water insoluble hydrophobic polymer (including waxes). Examples of suitable water soluble polymers include polyvinylpyrrolidine, hydroxypropyl cellulose, hydroxypropylmethyl cellulose, methyl cellulose, vinyl acetate copolymers, polysaccharides (such as alignate, xanthum gum, etc.) polyethylene oxide, methacrylic acid copolymers, maleic anhydride/methyl vinyl ether copolymers and derivatives and mixtures thereof. Examples of suitable water insoluble hydrophobic polymers include acrylates, cellulose derivatives such ethylcellulose or cellulose acetate, polyethylene, methacrylates, acrylic acid copolymers and high molecular weight polyvinylalcohols. Examples of suitable waxes include fatty acids and glycerides.

Preferably, the polymer is selected from hydroxypropyl cellulose, hydroxypropylmethyl cellulose, and methyl cellulose. More preferably, the polymer is hydroxypropylmethyl cellulose. Most preferably, the polymer is a high viscosity hydroxypropylmethyl cellulose with viscosity ranging from about 4,000 cps to about 100,000 cps. The most preferred high viscosity polymer is a hydroxypropylmethyl cellulose with a viscosity of about 15,000 cps, commercially available under the Tradename, Methocel, from The Dow Chemical Company.

The amount of the polymer in the dosage form generally varies from about 20% to about 50% by weight of the composition. Preferably, the amount of polymers varies from about 25% to about 45% by weight of the dosage form. Most preferably, the amount of polymer varies from about 30% to about 40% by weight of the dosage form.

The composition of the invention also typically includes pharmaceutically acceptable excipients. As is well known to those skilled in the art, pharmaceutical excipients are routinely incorporated into solid dosage forms. This is done to ease the manufacturing process as well as to improve the performance of the dosage form. Common excipients include diluents or bulking agents, lubricants, binders, etc. Such excipients are routinely used in the dosage forms of this invention.

Diluents, or fillers, are added in order to increase the mass of an individual dose to a size suitable for tablet compression. Suitable diluents include powdered sugar, calcium phosphate, calcium sulfate, microcrystalline cellulose, lactose, mannitol, kaolin, sodium chloride, dry starch, sorbitol, etc.

Lubricants are incorporated into a formulation for a variety of reasons. They reduce friction between the granulation and die wall during compression and ejection. This prevents the granulate from sticking to the tablet punches, facilitates its ejection from the tablet punches, etc. Examples of suitable lubricants include talc, stearic acid, vegetable oil, calcium stearate, zinc stearate, magnesium stearate, etc.

Glidant's are also typically incorporated into the formulation. A glidant improves the flow characteristics of the granulation. Examples of suitable glidant's include talc, silicon dioxide, and cornstarch.

Binders may be incorporated into the formulation. Binders are typically utilized if the manufacture of the dosage form uses a granulation step. Examples of suitable binders include povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Other excipients that may be incorporated into the formulation include preservatives, antioxidants, or any other excipient commonly used in the pharmaceutical industry, etc.

The amount of excipients used in the formulation will correspond to that typically used in a matrix system. The total amount of excipients, fillers and extenders, etc. varies from about 10% to about 40% by weight of the dosage form.

The matrix formulations are generally prepared using standard techniques well known in the art. Typically, they are prepared by dry blending the polymer, filler, valproate compound, and other excipients followed by granulating the mixture using an alcohol until proper granulation is obtained. The granulation is done by methods known in the art. The wet granules are dried in a fluid bed dryer, sifted and ground to appropriate size. Lubricating agents are mixed with the dried granulation to obtain the final formulation.

The compositions of the invention can be administered orally in the form of tablets, pills, or the granulate may be loose filled into capsules. The tablets can be prepared by techniques known in the art and contain a therapeutically useful amount of the valproate compound and such excipients as are necessary to form the tablet by such techniques. Tablets and pills can additionally be prepared with enteric coatings and other release-controlling coatings for the purpose of acid protection, easing swallow ability, etc. The coating may be colored with a pharmaceutically accepted dye. The amount of dye and other excipients in the coating liquid may vary and will not impact the performance of the extended release tablets. The coating liquid generally comprises film forming polymers such as hydroxypropyl cellulose, hydroxypropylmethyl cellulose, cellulose esters or ethers such as cellulose acetate or ethylcellulose, an acrylic polymer or a mixture of polymers. The coating solution is generally an aqueous solution or an organic solvent further comprising propylene glycol, sorbitan monoleate, sorbic acid, fillers such as titanium dioxide, a pharmaceutically acceptable dye.

A particularly preferred matrix system comprises: from about 50 weight percent to about 55 weight percent of a valproate compound; from about 20 weight percent to about 40 weight percent of hydroxypropyl methylcellulose; from about 5 weight percent to about 15 weight percent of lactose, from about 4 weight percent to about 6 weight percent of microcrystalline cellulose, and from about 1 weight percent to about 5 weight percent of silicon dioxide, in which said silicon dioxide has an average particle size ranging between about 1 micron and about 10 microns; and all weight percentages based upon the total weight of the dosage form.

This preferred embodiment of the invention also extends to a dry granular composition suitable for compressing into a tablet dosage form, the granular composition comprising particles of a size smaller than about 1 mm and comprising from about 50 weight percent to about 55 weight percent of an active ingredient selected from the group consisting of valproic acid, a pharmaceutically acceptable salt or ester of valproic acid, divalproex sodium, and valpromide; from about 20 weight percent to about 40 weight percent of hydroxypropyl methylcellulose; from about 5 weight percent to about 15 weight percent of lactose, from about 4 weight percent to about 6 weight percent of microcrystalline cellulose, and from about 1 weight percent to about 5 weight percent of silicon dioxide, in which said silicon dioxide has an average particle size ranging between about 1 micron and about 10 microns; and all weight percentages based upon the total weight of the granular composition.

More specifically, a divalproex matrix may be prepared by a) dry blending a mixture of from about 50 weight percent to about 55 weight percent divalproex sodium, from about 20 weight percent to about 35 weight percent hydroxypropylmethyl cellulose, from about 5 weight percent to about 15 weight percent lactose to form a uniform mixture of the dry ingredients; b) wet granulating the dry uniform mixture from step a); c) drying and sizing the wet granules from step b) to select granules having an average size below 1 mm; d) dry blending the granules with from about 4 weight percent to about 6 weight percent microcrystalline cellulose, and from about 1 weight percent to about 5 weight percent silicon dioxide having an average particle size ranging between about 1 micron and about 10 microns; and e) compressing the blended granules of step h) under a force ranging between about 2000 lbf (about $8.9 \times 10^3$ Newtons) and 10,000 lbf (about $4.45 \times 10^4$ Newtons). In a similar manner, the microcrystalline cellulose can be dry blended in step (a) with the divalproex sodium, hydroxypropyl methylcellulose and lactose.

II. Pharmacokinetic Profile

As noted above, the invention resides in the discovery that a matrix formulation meeting the dissolution profile above will simultaneously accomplish two results. First, it will provide a dosage form of valproate that will maintain therapeutic levels of the valproate ion over a 24 hour dosing period, thus providing once daily dosing. Secondly, it will reduce the incidence of side effects associated with valproate therapy. Formulations matching the dissolutions profiles above, will provide the pharmacokinetic profile described below.

In order to obtain these benefits, it is necessary for the once-a-day valproate dosage form to achieve certain pharmacokinetic parameters, when compared to a BID valproate dosage form. The qd dosage form must reduce peak plasma levels of valproate ("$C_{max}$") without significantly impacting either trough levels ("$C_{min}$") or the extent of valproate absorption ("AUC"). Further, the qd dosage form will exhibit a Degree of Fluctuation ("DFL") that is lower than that exhibited by a corresponding bid valproate dosage form.

$C_{max}$ for the qd dosage form should be statistically significantly lower than the $C_{max}$ for a bid dosage form of the same valproate compound, when each is measured at steady state in a fasting population. For example, a once-a-day divalproex sodium dosage form will exhibit a $C_{max}$ that is statistically significantly lower than that produced by a divalproex sodium delayed release tablet, when each is measured at steady state in a fasting population. Typically, peak plasma levels of valproate are reduced at least 10%. More typically, these peak plasma levels are reduced up to about 20%. This reduction must be accomplished with out any significant reduction in trough levels or total absorption of valproate.

$C_{min}$ for the qd dosage form should not be statistically significantly different from that obtained with a bid dosage form of the same valproate compound, when each is determined at steady state in a fasting population. More specifically, $C_{min}$ for a once-day divalproex sodium dosage form should not be statistically significantly different from that obtained with a delayed release divalproex sodium tablet when each is measured at steady state in a fasting population. Maintaining comparable trough levels to those obtained with the prior art bid dosage forms is necessary to maintain the therapeutic efficacy of the valproate compound. Inadequate trough levels are associated with seizures in epileptic patients.

In addition to reducing peak valproate levels as described above, it is also important that the total amount of valproate absorbed from the qd dosage form not be decreased significantly, when compared to a bid dosage form of the same valproate compound over a 24 hour dosing interval. Total drug absorption is also referred to as AUC (area under the curve). Methods for quantifying drug absorption are well known to those skilled in the art and have been standardized by the United States Food and Drug Administration at www.fda.gov/cder/guidance/stat-two.pdf, the contents of which are hereby incorporated by reference.

AUC for the qd dosage form will be equivalent to the AUC of the bid dosage form of the same valproate compound when each is measured at steady state in a fasting population over a 24 hour period. Equivalence of a pharmacokinetic parameter refers to the 90% confidence interval of the ratio of the central values of the pharmacokinetic parameter of the test formulation to the reference formulation being contained within 0.80 to 1.25. More specifically, the AUC of qd divalproex sodium dosage form will be equivalent to that obtained with a delayed release divalproex sodium tablet when each is determined at steady state in a fasting population over a 24 hour dosing period.

An AUC of at least 80% should be achieved with the formulations of this invention, when compared to a bid dosage form over a 24 hour interval. Values below 80% tend to negatively impact trough levels leading to sub-therapeutic concentrations of valproate and loss of epileptic control, etc. AUC's in excess of 125% should also be avoided. Thus with respect to the extent of absorption, the formulations of this invention should be considered equivalent to the corresponding bid valproate dosage form.

Degree of Fluctuation is a measurement of how much plasma levels of a drug vary over the course of a dosing interval. The closer the DFL is to zero (0), the less variance there is over the course of a dosing period. Thus a reduced DFL signifies that the difference in peak and trough plasma levels has been reduced. The DFL for a qd dosage form of this invention will be lower than that of the corresponding bid dosage form, for the same valproate compound, when each is evaluated at steady state in a fasting population. In a more specific embodiment, a qd divalproex sodium dosage form will have a DFL that is lower than that achieved with a bid delayed release divalproex sodium tablet when each is evaluated at steady state in a fasting population.

Despite the numerous therapeutic advantages of valproate therapy, certain patients consuming these medications experience side effects. For example, with divalproex sodium delayed release tablets, approximately 7% of patients report alopecia (hair loss), PDR supra, page 435–436. Up to 8% of patients report significant weight gain, PDR supra, page 435–436. Such side effects can have disasterous consequences for the self image of patients, especially for females, or younger patients. It is unknown whether this hair loss or weight gain is associated with obtaining or maintaining certain plasma levels of valproate.

Likewise, up to one-third of patients consuming divalproex sodium delayed release tablets complain of nausea. While such an event is certainly not life threatening, it is unpleasant for the patient. The nausea can lead to non-compliance and subsequent worsening of the patient's disease. Dizziness, tremor, asthenia, somnolence are also common with valproate therapy. The impact of plasma levels on these side effects is also unknown. For a more complete discussion of valproate side effects, please refer to PDR supra, page 435–436.

The incidence of these side effects can be reduced significantly by reducing peak plasma levels of valproate by approximately 10–20%. Further, therapeutic control can be maintained by meeting the $C_{min}$ DFL and AUC guidelines discussed above. Such a finding was totally unexpected. The literature clearly documents that the correlation between side effects and plasma valproate levels is unknown. Formulations meeting the dissolution profiles above will exhibit this reduced incidence of side effects.

The following examples are presented in order to further illustrate the invention. These examples should not be construed in any manner to limit the invention.

EXAMPLES

Example 1

The following example provides a summary of the experimental work culminating in the formulation of the present invention. It also discloses a dissolution method which does not correlate with an in-vivo/in-vitro correlation profile.

One gram tablets containing 538 mg of divalproex sodium, magnesium stearate, dicalcium phosphate, microcrystalline cellulose (Avicel®, FMC Corporation, Philadelphia, Pa., USA) and/or lactose and various hydrophilic polymers were prepared. Hydrophilic polymers tested included hydroxypropyl methylcellulose, methylcellulose (Methocel° grades K100LVP CR, K4MP CR, K15MP CR and K100MP CR, Dow Chemical, Midland, Mich., USA); hydroxypropyl cellulose (Klucel® LF, Hercules, Inc., Wilmington, Del., USA); and alginate (Keltone® grades LVCR and HVCR, Kelco Co., San Diego, Calif., USA).

Bulk drug was milled prior to use and was sized to pass a 40 mesh sieve (0.42 mm nominal mesh opening). The milled and sieved bulk drug was dry-mixed with polymer and excipients in a Collette Gral 10 high shear mixer for 5 min at a high chopper speed of 3000 rpm and impeller speed of 200 rpm. Granules were prepared by adding 70 ml/kg of granulation fluid (water or water/ethanol mixtures) to the polymer/drug/excipient powder mixture over a 1–2 minute period at high chopper speed of 3000 rpm and impeller speed of 500 rpm. Additional fluid of 10–165 ml was added in one step as needed in order to reach granulation end-point. Total granulation time ranged from 2–18 min.

Tablet matrix ingredients included microcrystalline cellulose, lactose, magnesium stearate, and silicon dioxide. The resulting granules were tray dried at 50° C.–55° C. overnight under reduced pressure. The dried granules were mixed with lubricant (magnesium stearate) in a bag and then passed through a 20 mesh (0.84 mm nominal opening) sieve. Tablets weighing 1 g were pressed in a Model C Carver Press tableting machine using a 0.747 inch (1.9 cm)×0.360 inch (0.91 cm) ovaloid die at a compression force between about 2000 lbf (about $8.9 \times 10^3$ Newtons) and about 10,000 lbf (about $4.45 \times 10^4$ Newtons), preferably between about 2300 lbf ($1.02 \times 10^4$ Newtons) to about 5000 lbf ($2.25 \times 10^4$ Newtons). The tablet compositions are presented in Table 1.

TABLE 1

Test Divalproex Matrix Tablet Formulations

| Ingredient[1] | A | B | C | D | E | F | G | H | I |
|---|---|---|---|---|---|---|---|---|---|
| Divalproex sodium | 50 | 50 | 50 | 50 | 50 | 53.8 | 53.8 | 53.8 | 53.8 |
| Methocel ® K100LVPCR | 18 | 20 | — | — | — | — | — | — | 10 |
| Methocel ® K4MPCR | 8 | — | — | — | — | — | — | — | — |
| Klucel ® LF | — | 20 | — | — | — | — | — | — | — |
| Keltone ® HVCR | — | — | 30 | — | — | — | — | — | — |
| Methocel ® K15MPCR | — | — | — | — | 30 | 26 | 35 | — | 16 |
| Methocel ® K100MPCR | — | — | — | 15 | — | — | — | 30 | — |
| Lactose | 23 | 9.5 | 9.5 | 29.5 | 14.5 | 14.7 | 5.7 | 10.7 | 14.7 |
| Avicel ® PH101 | — | 0 | 5 | 5 | 5 | 5 | 5 | 5 | 5 |
| PVP[2] | — | — | 5 | — | — | — | — | — | — |
| Magnesium Stearate | 1 | 0.5 | 0.5 | 0.5 | 0.5 | 0.5 | 0.5 | 0.5 | 0.5 |

[1]Percent by weight, based upon the total tablet weight
[1]Poly(vinylpyrolidone)

Initial Formulation Screening

Initial screening of the matrix tablet formulations was performed using a number of tests. Tablet hardness for each formulation was measured using a Model VK2000 VanKel tablet hardness analyzer and recorded in units of kiloPounds (kP) as the average of ten trials.

Friability of the tablets were tested by rotating the tablets samples 100 times using a Erweka TA friabilator. Friability of tablets for each formulation were calculated based on the weight loss of the tablets in this test.

Bulk density of the formulation granules was measured by carefully filling a glass graduated cylinder to the 100 ml mark. Tap density was determined following 100 taps of the filled cylinder.

Determination of granule size distribution was performed by collecting granules larger than 140 mesh (about 0.105 mm nominal mesh opening) and 40 mesh (about 0.42 mm nominal mesh opening) for evaluation of the percentage of fines and large granules.

In vitro dissolution tests were conducted using Apparatus II described in the United State Pharmacopeia XXI/National Formulary XVI. Samples aliquots of 1.5 ml were withdrawn and filtered through a 0.45 μm filter and assayed by TDX® fluorescent polarization immunoassay. Upon withdrawal of each sample, an equal volume of medium was added to the test mixture to maintain constant volume. The test conditions were as follows:

| | |
|---|---|
| Apparatus | USP II, paddle |
| Medium | 1M HCl for one hour; remaining time pH 6.8 buffer |
| Volume of medium | 900 ml |
| Temperature | 37° C. ± 0.5° C. |
| Paddle speed | 100 rpm |
| Sampling volume | 1.5 ml |
| Sampling times | 0, 0.5, 1, 2, 4, 6, 8, 13, 24 hours |

The results of these tests are presented in Table 2.

Based upon these initial studies, and the data appearing in Table 2 above, the following conclusions were drawn:

(1) Effects on tablet hardness: The use of ethanol as a granulation fluid tends to increase tablet hardness. There is a strong interaction between ethanol and particle size of the bulk drug. The increase in hardness was only observed for formulations containing drug of larger particle size. The opposite effect was found for drug of smaller particle size.

(2) Effects on friability: The use of drug having a small particle size reduced friability. However, this effect was significant only for formulations using water as granulation fluid.

(3) Effects on density: The use of ethanol as a granulation fluid was shown to decrease the density of the granules. However, significant interactions of ethanol with the use of Klucel®, and of ethanol with drug particle size were observed. Ethanol decreased the density only of formulations containing drug of larger particle size and/or formulations without Klucel® present. The opposite effects were found for formulations containing smaller drug particles and/or Klucel®. The same conclusions were obtained with either tap or bulk density as response.

(4) Effects on size of granules: More granules of larger size were obtained with the use of drug having a larger particle size. Moreover, interaction between ethanol and Klucel® was found to be significant i.e. use of ethanol tends to generate larger granules when there is no Klucel® present in the formulation. No effect was observed for formulations containing 4% Klucel®. Factors that showed significant influences on the percentage of fines in the granules included ethanol, drug particle size, and their interaction. Using smaller drug particles tended to yield more fines in the granules. More fines were generated when ethanol was used as a granulation fluid. The effect of ethanol was most significant for formulations containing drug of a small particle size.

(5) Effects on granulation fluid volume: In order to obtain granulation end-point, more fluid volume was needed for formulations containing either drug of a smaller particle size or with the use of ethanol as granulation fluid.

(6) In vitro drug release: In vitro percent release of valproic acid from controlled-release tablets are shown in FIG. 1. The difference in release profiles among formulations was small. In the study, percent release at 8 hours ($Q_{8hr}$) was used to represent release rate for data analysis. It was found that the use of Klucel® or drug of a larger particle size in the formulation resulted in an increase in release rate. Similar results were obtained when $Q_{10hr}$ or $Q_{24hr}$ was used to estimate the release rate.

Formulations containing high load and high viscosity grades of polymers often showed poor compressibility. This is believed to be the result of the increase in polymer order and elasticity with increasing molecular weight. Hardness of the tablets remained almost unchanged under compression forces ranging from about 3000 lb ($1.3 \times 10^4$ Newtons) to about 10,000 lb ($4.45 \times 10^4$ Newtons).

TABLE 2

| Formulation | Granulating Fluid Volume | Hardness (kP) | Friability (% Loss) | Tap Density (g/ml) | Bulk Density (g/ml) | % Granule Size >40 Mesh | Fines[1] | $Q_{8\,hr}$ (%)[2] |
|---|---|---|---|---|---|---|---|---|
| A | 100 | 11.9 | 0.049 | 0.504 | 0.429 | 22.6 | 6.1 | 27.6 |
| B | 80 | 7.2 | 0.16 | 0.515 | 0.438 | 31.3 | 9.8 | 29.0 |
| C | 115 | 12.2 | 0.025 | 0.459 | 0.39 | 30.2 | 3.3 | 28.6 |
| D | 80 | 8.4 | 0.162 | 0.459 | 0.406 | 38.2 | 6.6 | 30.4 |
| E | 235 | 10.4 | 0.060 | 0.599 | 0.509 | 21.5 | 40.7 | 27.0 |
| F | 110 | 12.2 | 0.006 | 0.400 | 0.340 | 49.2 | 1.8 | 28.0 |
| G | 200 | 9.4 | 0.085 | 0.596 | 0.506 | 24.0 | 29.7 | 29.7 |
| H | 150 | 12.9 | 0.142 | 0.593 | 0.504 | 35.0 | 22.8 | 30.0 |
| I | 130 | 9.5 | 0.015 | 0.475 | 0.404 | 33.8 | 1.2 | 28.8 |

[1] Defined as percent granules passing a 0.105 mm nominal mesh opening
[2] Defined as percent drug released in an 8-hour period under the in vitro test conditions In order to increase the hardness of tablets, microcrystalline cellulose and colloidal silicon dioxide were tested by externally adding small amounts to the granules at levels of 1–5%. Table 3 shows the results from the test. It was found that external addition of small amounts of microcrystalline cellulose or colloidal silicon dioxide significantly increased tablet hardness.

TABLE 3

Effect of External Addition of Microcrystalline Cellulose or Silicon Dioxide

| Hardness Test Formulation | Additive | Hardness (kP) |
|---|---|---|
| Ia | None | 6.2 |
| Ib | 5% Avicel ® | 9.6 |
| Ic | 5% Avicel ® and 1% silicon dioxide[1] | 13.8 |
| IIa | None | — |
| IIb | 1% Silicon dioxide[1] | 10.9 |
| IIc | 5% Avicel ® and 1% silicon dioxide[1] | 14.4 |
| IIIa | None | 5.8 |
| IIIb | 1% Silicon dioxide[1] | 10.8 |
| IIIc | 5% Avicel ® and 1% silicon dioxide[1] | 14.8 |

[1]Silicon dioxide was Cab-O-Sil M-5 fumed silica (Cabot Corp., Boyertown, PA, USA) having average particle size of between about 0.2 and 0.3 microns As shown by the data in Table 3, the addition of either 1% silicon dioxide or 5% microcrystalline cellulose to the hydrophilic matrix formulations of the invention almost doubled tablet hardness, while adding both resulted in a greater than doubling of tablet hardness. However, although the results shown above demonstrated improvement of tablet hardness by the combined use of the external addition of Avicel® microcrystalline cellulose and Cab-o-sil® silicon dioxide, problems of sticking and relatively low density persisted. The low bulk density (i.e. 40 g/l) of the small particle size Cab-O-Sil® fumed silica led to the problem of not being able to load sufficient material into the tablet die.

In response to this problem, a different silicon dioxide having a larger average particle size ranging from about 1 micron to about 10 microns, preferably ranging between about 2 microns to about 5 microns, and most preferably about 2–3 microns was used. One such material is available as Syloid® 244, available from W. R. Grace, Lexington, Mass., USA. When this material was used, initially intended as a de-tackifying and hardening agent for tableting, a surprising and unexpected benefit was conferred upon the formulation, as shown below. The material was added "externally" to the formulation: that is, the active ingredient, polymer(s) and excipients were dry blended, wet granulated, and then dried and sized. The silicon dioxide was then added to the granular formulation and the resulting mixture blended prior to pressing into tablets.

Figure 2:
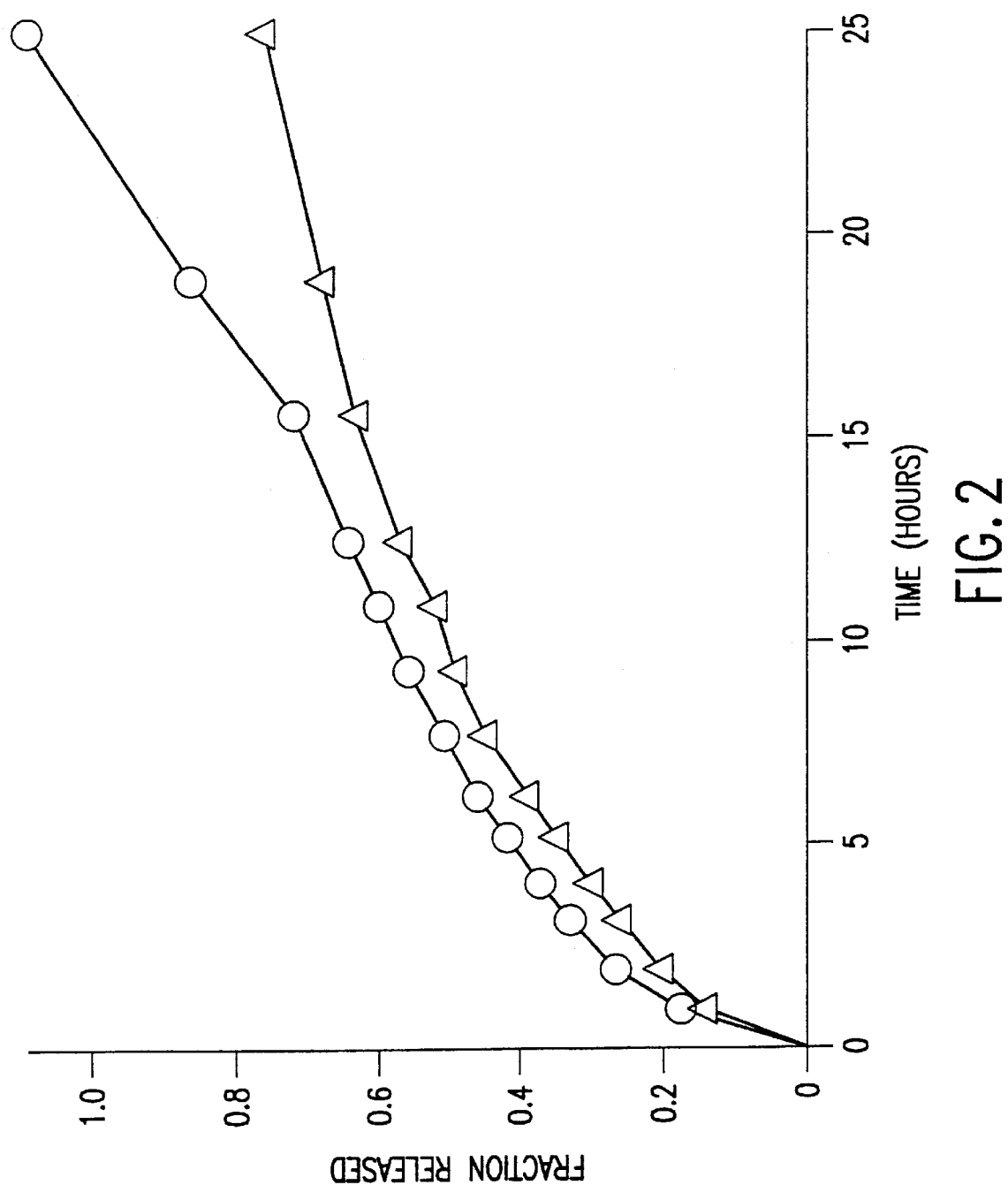
FIG. 2 is a graphical representation of in vitro release of drug from two preferred controlled release tablet formulations of the invention.

On the basis of the above findings, preferred tablet formulations were chosen for an in vivo absorption study in healthy human subjects. The ingredients of the formulations and in vitro release rates are shown in Table 4 and FIG. 2, respectively. The formulations were designed to have different release rates by using high viscosity HPMC alone or blended with low viscosity HPMC. The target in vitro release rates were chosen to release drug in vivo for 16–20 hours. Formulation B was subsequently used in the pharmacokinteic studies and clinical trail described in Examples 4–6 of this application.

TABLE 4

Preferred Controlled Release Formulations of the Invention

| Ingredient | Formulation A | Preferred Formulation B |
|---|---|---|
| Divalproex sodium (milled)[1] | 53.82%[2] | 53.82% |
| Hydroxypropyl methylcellulose (Methocel ® K15M, CR) | 8% | 30% |
| Methyl cellulose (Methocel ® K100L, CR) | 18% | — |
| Anhydrous lactose | 12.18% | 8.18% |
| Microcrystalline cellulose (Avicel ® PH 101) | 5% | 5% |
| Silicon dioxide (Average particle size 1 µm< >10 µm) (Syloid ® 244) | 3% | 3% |
| Total tablet weight | 1 g | 1 g |

[1]Bulk drug sized to pass a 40 mesh sieve (0.42 mm nominal mesh opening
[2]All percentages in the Table expressed as weight percentages based upon the total weight of the tablet Example 2

This Example illustrate the manufacture of a preferred dosage form of the present invention at a larger scale.

Divalproex sodium was milled through a 0.040" band with impact forward (flat edge) using a Fluid Air Mill operating at 50–75 rpm feed rate and 3500 rpm mill speed. 81 kg of milled drug was vacuum loaded directly into the Collette Gral-600 high shear mixer and mixed with 12.3 kg of lactose, 7.5 kg of microcrystalline cellulose and 45 kg of hydroxypropylmethycellulos for 5 minutes. The mixture of drug and excipients was granulated using 18 kg of purified water for a total of 7 minutes and dried in a fluid bed dryer until the average moisture content of the granules, measured by a gravimetric test, is below the in-process control limit of 1.0% w/w. The dried granules are sized using a speed sifter and the oversize granules are milled through a 0.078" band with impact forward (flat edge) using a Fluid Air Mill operating at 50 rpm feed rate and 3500 rpm mill rate. The two fractions of granules are then recombined and blended with 4.5 kg of silicon dioxide in a twin-shell blender. The blended mixture is compressed into 1.00 gram tablets with approximately 0–12 kN precompression and 24 kN main compression force using a rotary tableting machine (Fette 2090) operating at 35–50 rpm.

Example 3

Multiple Dose Study

The bioavailability and plasma concentration versus time profile of valproate from an oral extended-release tablet formulation of divalproex sodium (made as in Example 2) determined under fasting and nonfasting conditions was compared to those of a commercially available enteric coated divalproex sodium delayed-release tablet formulation (Depakote®, Abbott Laboratories; reference) determined under fasting conditions in healthy subjects. The study was conducted according to a multiple-dose, open-label, three-period, randomized, complete crossover design. In each period, a six-day regimen was administered with a minimum of 16 days separating the first doses of consecutive periods. The three regimens were:

Regimen A: Extended-release formulation 1000 mg q24 h administered under fasting conditions (test/invention)

Regimen B: Extended-release formulation 1000 mg q24 h administered 30 minutes after breakfast was served (test/invention)

Regimen C: Depakote enteric coated tablet 500 mg q12 h administered under fasting conditions (reference/bid comparator)

A schedule of the doses and meal times for the three regimens follows.

TABLE 5

| Regimen | Formulation | Time of Dose | Breakfast | Lunch | Dinner | Snack |
|---|---|---|---|---|---|---|
| A | Test ER | 6:00 a.m. | 8:00 a.m. | 12 N | 8:00 pm | 10:30 pm |
| B | Test ER | 6:00 a.m. | 5:30 a.m. | 12 N | 8:00 pm | 10:30 pm |
| C | Reference DR | 6:00 a.m. 6:00 p.m. | 8:00 a.m. | 12 N | 8:00 pm | 10:30 pm |

ER = Extended-Release; DR = Delayed Release (enteric-coated).

Fourteen healthy adult subjects (11 male and 3 female subjects) completed all phases of the study. The mean age was 27 years (range 19–51 years), mean height was 69 inches (range 63–74 inches) and weight was 161 pounds (range 120–200 pounds).

Blood samples (7 mL) were collected at 0, 12, 24, 36, 48, 60, 72, 84, 96, 108, 120, 121, 122, 123, 124.5, 126, 127.5, 129, 130.5, 132, 133, 134, 135, 136.5, 138, 139.5, 141, 142.5 and 144 hours after the first dose of each period. Plasma samples were analyzed for valproic acid using a validated gas-liquid chromatographic method with flame ionization detection at Oneida Research Services, Inc., Whitesboro, N.Y.

Pharmacokinetic and Statistical Analyses

Pharmacokinetic parameters were estimated by noncompartmental techniques. For Day 6 data, these included $C_{max}$, $T_{max}$, $C_{min}$, $AUC_{0-24}$, and degree of fluctuation (DFL). If $C_{max}$ for the reference occurred after the second dose of Day 6, $T_{max}$ was taken to be the time since the second dose rather than the time from the first dose.

Analyses of variance (ANOVAs) appropriate for crossover models were performed for $T_{max}$, DFL, and for the natural logarithms of $C_{min}$, $C_{max}$, and $AUC_{0-24}$. Within the framework of the ANOVA, the regimens were compared pair-wise, each comparison done by a test at significance level of 0.05. Equivalence of the two formulations with respect to AUC was addressed by performing the two one-sided tests procedure at significance level 0.05 within the framework of the ANOVA on the logarithm of AUC. As a further aid for assessing the characteristics of the ER formulation, 95% confidence intervals for the ratios of the ER formulation central values to the reference regimen central value were obtained from the ANOVAs for logarithms of $C_{min}$ and $C_{max}$. In addition, a two one-sided tests procedure was carried out to compare the fasting and nonfasting extended-release formulation regimens.

Figure 3:
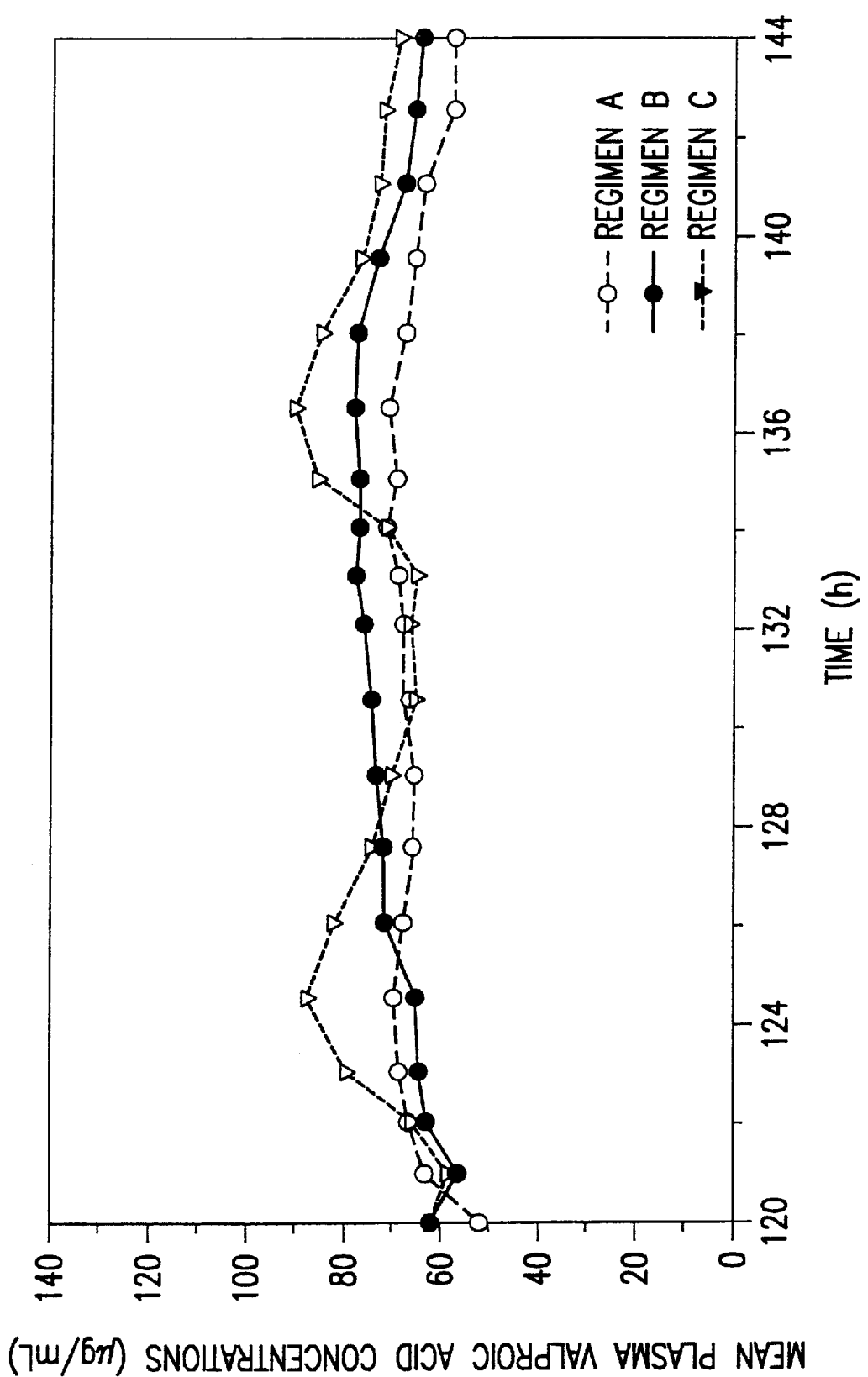
FIG. 3 is a graphical representation of plasma valproate levels of two qd (once-a-day) and one bid (twice-a-day) dosage form.

The mean valproic acid plasma concentration-time profiles for the three regimens are shown in FIG. 3.

The pharmacokinetic results for Day 6 of each regimen are summarized in the following Table 6.

TABLE 6

| | Mean (Standard Deviation), n = 14 | | | | |
|---|---|---|---|---|---|
| Regimen | $T_{max}$ (hr) | $C_{max}$ (µg/mL) | $C_{min}$ (µg/mL) | $AUC_{0-24}$ (µg · hr/mL) | DFL |
| A | 13.6 (6.3)* | 80.5 (18.6)* | 48.2 (17.0) | 1592 (402) | 0.523 (0.231) |
| B | 15.9 (4.5)* | 85.0 (12.5)* | 55.1 (13.3) | 1709 (276) | 0.432 (0.127)* |
| C | 3.6 (0.9) | 99.4 (15.7) | 54.1 (13.1) | 1789 (332) | 0.623 (0.160) |

*Statistically significantly different from Regimen C.
Regimen A: Divalproex Sodium ER; 2 × 500 mg once daily, fasting.
Regimen B: Divalproex Sodium ER; 2 × 500 mg once daily, nonfasting.
Regimen C: Depakote Tablet; 500 mg twice daily, fasting.

The mean $T_{max}$ for Regimens A and B were about three-fold longer than that of Regimen C. The differences in $T_{max}$ between Regimens A and C and between B and C were statistically significant. Regimens A and B tended to have lower $C_{max}$ than that of Regimen C, and these differences were statistically significant. The regimens did not differ statistically significantly with respect to $C_{min}$. The mean DFL for both ER Regimens A and B was lower than that of the reference, and the difference between Regimen B and the reference was statistically significant.

The 95% confidence intervals for bioavailability of the ER regimens relative to the reference for $C_{max}$ and $C_{min}$ are given below. The point estimate for the ratio of the central values for both $C_{max}$ and $C_{min}$ for Regimen A, and $C_{max}$ for Regimen B, were lower than 1.0. The point estimate of the ratio for $C_{min}$ for Regimen B was approximately unity.

TABLE 7

| | | Relative Bioavailability | | | |
|---|---|---|---|---|---|
| | | $C_{max}$ | | $C_{min}$ | |
| Regimen | | | 95% | | 95% |
| Test | Reference | Point Estimate | Confidence Interval | Point Estimate | Confidence Interval |
| A | C | 0.811 | 0.742–0.887 | 0.847 | 0.672–1.067 |
| B | C | 0.861 | 0.788–0.941 | 1.026 | 0.814–1.293 |

Regimen A: Divalproex Sodium ER; 2 × 500 mg once daily, fasting.
Regimen B: Divalproex Sodium ER; 2 × 500 mg once daily, nonfasting.
Regimen C: Depakote Tablet; 500 mg twice daily, fasting.

The results for the two one-sided tests procedure for equivalence assessment of the regimens via a 90% confidence interval based on the natural logarithm of $AUC_{0-24}$ are given below.

TABLE 8

Two One-Sided Tests Procedure for Equivalence Assessment, Day 6 AUC

| | | Relative Bioavailability | |
|---|---|---|---|
| Test | Reference | Point Estimate | 90% Confidence Interval |
| A | C | 0.891 | 0.817–0.971 |
| B | C | 0.970 | 0.890–1.058 |
| A | B | 0.918 | 0.842–1.001 |

Regimen A: Divalproex Sodium ER; 2 × 500 mg once daily, fasting.
Regimen B: Divalproex Sodium ER; 2 × 500 mg once daily, nonfasting.
Regimen C: Depakote Tablet; 500 mg twice daily, fasting.

The 90% confidence intervals for AUC on Day 6 for the test ER formulation administered under fasting (A) and nonfasting (B) conditions versus the reference fasting (C), both satisfied the 0.80–1.25 criterion for equivalence. Additionally, the 90% confidence interval for the ratio of central values of AUC for the test ER formulation fasting-:nonfasting regimens also satisfied the equivalence criterion.

The extended-release formulation performs well. The extended-release regimens are equivalent to the reference regimen with respect to extent of absorption as characterized by AUC. The two test regimens did not differ statistically significantly from the reference regimen with respect to $C_{min}$. The lower $C_{max}$ and later $T_{max}$ central values of the extended-release regimens compared the reference regimen suggest that the ER formulation provides extended release of valproic acid in vivo under fasting and nonfasting conditions. The mean DFL for the extended-release formulation administered under nonfasting conditions is lower (~31%) than that of the reference regimen (observed means of 0.432 and 0.623, p<0.05). The mean DFL for the extended-release formulation administered under fasting conditions was also lower (~16%) than that of the reference regimen although statistical significance was not attained (observed means of 0.523 and 0.623, p=0.126).

Example 4
Multiple Dose Study

The bioavailability and plasma concentration-time profile of valproic acid from a new oral extended-release tablet formulation of divalproex sodium (invention, made as in Example 2) was compared to that from the currently marketed divalproex sodium enteric-coated delayed-release tablet (Depakote® Abbott Laboratories; reference) under multiple-dose conditions.

Sixteen subjects enrolled in the study. They had a mean age of 34 years (range 19–55 years), mean height of 69 inches (range 65–75 inches), and mean weight of 180 pounds (range 148–209 pounds). This was a multiple-dose, open-label, 2-period, crossover study with no washout between periods in healthy adult male and female subjects comparing the extended-release (ER/invention) test formulation (2×500 mg qd) with the delayed-release (DR/bid/prior art) Depakote enteric-coated tablet (500 mg q12 h) as the reference. In one part of the study (Groups I and II), 4 subjects started on the ER test tablet in the morning and switched over to the 500 mg DR tablet bid on Day 7 (end of Period 1) and continued on it through Day 12 (Period 2). The other four subjects (Group II) started with the DR tablet and switched over to the ER test tablet in the morning of Day 7 and continued through Day 12. The second part of the study (Groups III and IV) was a repeat of the first part except that the test formulation was given in the evening instead of in the morning. The ER formulation was administered after a meal, and the DR tablet was given under fasting conditions.

A schematic of the formulations administered and the meal times follows.

TABLE 9

| Formulation | Time of Dose | Breakfast | Lunch | Dinner | Snack |
|---|---|---|---|---|---|
| Morning Dose for ER Formulations | | | | | |
| ER | 6 am | 5:30 am | 12 N | 5:30 pm | 10:30 pm |
| DR | 6 am, 6 pm | 8:00 am | 12 N | 8:00 pm | 10:30 pm |

TABLE 9-continued

| Formulation | Time of Dose | Breakfast | Lunch | Dinner | Snack |
|---|---|---|---|---|---|
| Evening Dose for ER Formulations | | | | | |
| ER | 6 pm | 5:30 am | 12 N | 5:30 pm | 10:30 pm |
| DR | 6 pm, 6 am | 8:00 am | 12 N | 8:00 pm | 10:30 pm |

ER = Extended-Release (invention); DR = Delayed-Release (prior art).

Regimens: The regimens administered were as follows.
  A: Divalproex sodium extended-release tablets, 500 mg valproic acid equivalents; 2×500 mg tablets once every 24 hours starting with a morning dose. (invention)
  B: Divalproex sodium enteric-coated delayed-release tablets (same as Depakote, Abbott Laboratories, reference); one 500 mg tablet once every 12 hours starting with a morning dose.
  C: Divalproex sodium extended-release tablets, 500 mg valproic acid equivalents; 2×500 mg tablets once every 24 hours starting with an evening dose. (invention)
  D: Divalproex sodium enteric-coated delayed-release tablets (same as Depakote, Abbott Laboratories, reference; one 500 mg tablet once every 12 hours starting with an evening dose.

Blood samples (7 mL) were taken at 0, 12, 24, 36, 48, 60, 72, 84, 96, 108, 120, 121, 122, 123, 124.5, 126, 127.5, 129, 130.5, 132, 133, 134, 135, 136.5, 138, 139.5, 141, 142.5 and 144 hours from the first dose of each period. Blood samples were taken on the same schedule for Groups III and IV except that they were 12 hours later than for Groups I and II (i.e., first blood sample at 6 p.m. instead of 6 a.m.). Plasma samples were analyzed for valproic acid using a validated gas-liquid chromatographic method with flame ionization detection at Oneida Laboratories, New York.

Pharmacokinetic and Statistical Analyses

Pharmacokinetic parameters were estimated by noncompartmental techniques. For Day 6 and 12 data, $C_{max}$, $T_{max}$, $C_{min}$, $AUC_{0-24}$ and DFL were calculated. If $T_{max}$ occurred after the second dose of Day 6 or 12, $T_{max}$ was taken to be the time since the second dose rather than the time from the first dose.

Analyses of variance (ANOVAs) were performed for $T_{max}$, DFL, and for the natural logarithms of $C_{min}$, $C_{max}$, and $AUC_{0-24}$. The model had effects for time (whether subject received ER formulation in morning or evening), formulation sequence, subjects nested within time by formulation sequence, formulation period, and the interaction of time with each of formulation sequence, formulation and period. Subject effects were random and all other effects were fixed. Equivalence of the two formulations with respect to AUC was addressed by performing the two one-sided tests procedure within the framework of the ANOVA on the logarithm of AUC. This confidence interval for relative bioavailability was obtained by exponentiating the endpoints of a 90% confidence interval for the difference of logarithm means (difference of formulation main effects). As a further aid for assessing the characteristics of the ER formulation, 95% confidence intervals for bioavailability relative to that of the reference formulation were obtained from the ANOVAs for logarithms of $C_{min}$ and $C_{max}$.

The mean plasma valproic acid concentrations following administration of the 1000 mg test formulation once every 24 hours (Regimens A and C) or the 500 mg reference formulation once every 12 hours (Regimens B and D) for Days 6 and 12 are shown in FIG. 4.

The pharmacokinetic results for Day 6 of each regimen are summarized in the following table.

TABLE 10

| Regimen | | $C_{max}$ (µg/mL) | $C_{min}$ (µg/mL) | $AUC_{0-24}$ (µg · hr/mL) | DFL |
|---|---|---|---|---|---|
| ER formulation in morning (n = 8) | | | | | |
| A | 0–24 hr | 87 (17.3) | 55.5 (38.7) | 1771 (22.8) | 0.46 (55.9) |
| B | 0–24 hr | 102 (10.5) | 53.3 (26.2) | 1798 (16.6) | 0.67 (31.2) |
| ER formulation in evening (N = 8) | | | | | |
| C | 0–24 hr | 85 (10.0) | 57.4 (14.9) | 1728 (12.5) | 0.39 (19.7) |
| D | 0–24 hr | 98 (10.2) | 54.7 (13.9) | 1747 (10.5) | 0.60 (12.3) |
| All groups combined | | | | | |
| A and C | 0–24 hr | 86 (13.8) | 56.4 (28.1) | 1749 (17.9) | 0.42 (44.3) |
| B and D | 0–24 hr | 100 (10.3) | 54.0 (20.2) | 1773 (13.6) | 0.64 (24.8) |

Regimen A: Divalproex Sodium ER; 2 × 500 mg in a.m., nonfasting.
Regimen B: Depakote DR Tablet; 500 mg in a.m. and 500 mg in p.m., fasting.
Regimen C: Divalproex Sodium ER; 2 × 500 mg in p.m., nonfasting.
Regimen D: Depakote DR Tablet; 500 mg in p.m. and 500 mg in a.m., fasting.

There were no statistically significant differences in the pharmacokinetic results between subjects who received the ER formulation in the morning and those who received the ER formulation in the evening. Hence, the conclusions are based on the combined data of the groups.

The mean DFL of the ER formulation was statistically significantly lower than that of the reference. The two formulations differed statistically significantly with respect to $C_{max}$, but not with respect to $C_{min}$ and AUC. For $C_{max}$ and $C_{min}$, the 95% confidence interval for bioavailability of the ER formulation relative to that of the reference was 0.80 to 0.91 and 0.89 to 1.18, respectively. The 90% confidence interval by which the two one-sided tests procedure was performed for AUC was 0.924 to 1.041, being entirely within the equivalence range of 0.80 to 1.25.

Mean $C_{max}$ for the test formulation on Day 6 for both periods, when the plasma valproic acid concentrations were characterized, was lower than the reference formulation and was statistically significantly different. Mean $AUC_{0-24}$ for Day 6 of each period was not significantly different between the test and reference formulations. Relative bioavailability based on the ratio (test:reference) of mean logarithm of $AUC_{0-24}$ (90% confidence interval) was 0.981 (0.924 to 1.041). The degree of fluctuation was statistically significantly smaller for the test formulation (0.42) than for the reference (0.64). The results demonstrate the extended-release characteristics of the test formulation and its similarity in bioavailability based on AUC when compared to the reference formulation.

Example 5

Based on the results of one multicenter, randomized, double-blind, placebo-controlled clinical trial, the formulation of Example 2 (hereinafter "Depakote ER") was well tolerated in the prophylactic treatment of migraine headache. Of the 122 patients exposed to Depakote ER in the placebo-controlled study, 8% discontinued for adverse events, compared to 9% for the 115 placebo patients.

a. Invention

The study below describes the side effect profile of a qd divalproex sodium dosage form according to this invention.

Table 11 includes those adverse events reported for patients in the placebo-controlled trial where the incidence rate in the Depakote ER-treated group was greater than 5% and was greater than that for placebo patients.

TABLE 11

Adverse Events Reported by >5% of Depakote Extended Release (ER/Invention) Patients During the Migraine Placebo-Extended Trial with a Greater Incidence than Patients Taking Placebo[1]

| Body System Event | Depakote ER (N = 122) | Placebo (N = 115) |
|---|---|---|
| Gastrointestinal | | |
| Nausea | 15% | 9% |
| Dyspepsia | 7% | 4% |
| Diarrhea | 7% | 3% |
| Vomiting | 7% | 2% |
| Abdominal Pain | 7% | 5% |
| Nervous System | | |
| Somnolence | 7% | 2% |
| Other | | |
| Infection | 15% | 14% |

[1]The following adverse events occurred in greater than 5% of Depakote ER-treated patients and at a greater incidence for placebo than for Depakote ER: asthenia and flu syndrome.

The following additional adverse events were reported by greater than 1% but not more than 5% of Depakote ER-treated patients and with a greater incidence than placebo in the placebo-controlled clinical trial for migraine prophylaxis:

Body as a Whole: Accidental injury, viral infection.
Digestive System: Increased appetite, tooth disorder.
Metabolic and Nutritional Disorders: Edema, weight gain.
Nervous System: Abnormal gait, dizziness, hypertonia, insomnia, nervousness, tremor, vertigo.
Respiratory System: Pharyngitis, rhinitis.
Skin and Appendages: Rash.
Special Senses: Tinnitus.

b. Prior Art

The study below describes the side effect profile of Depakote DR.

Based on two placebo-controlled clinical trials and their long term extension, Depakote DR tablets were generally well tolerated with most adverse events rated as mild to moderate in severity. Of the 202 patients exposed to Depakote DR tablets in the placebo-controlled trials, 17% discontinued for intolerance. This is compared to a rate of 5% for the 81 placebo patients. The adverse events reported as the primary reason for discontinuation by greater than or equal to 1% of 248 Depakote DR-treated patients were alopecia (6%), nausea and/or vomiting (5%), weight gain (2%), tremor (2%), somnolence (1%), elevated SGOT and/or SGPT (1%), and depression (1%).

Table 12 includes those adverse events reported for patients in the placebo-controlled trials where the incidence rate in the Depakote DR-treated group was greater than 5% and was greater than that for placebo patients.

TABLE 12

Adverse Events Reported by >5% of
Depakote DELAYED-RELEASE (DR/priorart)
Patients During Migraine Placebo-Extended Trials with a Greater
sIncidence than Patients Taking Placebo[1]

| Body System Event | Depakote DR (N = 202) | Placebo (N = 81) |
|---|---|---|
| Gastrointestinal System | | |
| Nausea | 31% | 10% |
| Dyspepsia | 13% | 9% |
| Diarrhea | 12% | 7% |
| Vomiting | 11% | 1% |
| Abdominal Pain | 9% | 4% |
| Increased Appetite | 6% | 4% |
| Nervous System | | |
| Asthenia | 20% | 9% |
| Somnolence | 17% | 5% |
| Dizziness | 12% | 6% |
| Tremor | 9% | 0% |
| Other | | |
| Weight Gain | 8% | 2% |
| Back Pain | 8% | 6% |
| Alopecia | 7% | 1% |

[1]The following adverse events occurred in greater than 5% of Depakote DR-treated patients and at a greater incidence for placebo than for Depakote DR: flu syndrome and pharyngitis.

The following additional adverse events not referred to above were reported by greater than 1% but not more than 5% of Depakote DR-treated patients and with a greater incidence than placebo in the placebo-controlled clinical trials:

Body as a Whole: Chest pain.

Cardiovascular System: Vasodilatation.

Digestive System: Constipation, dry mouth, flatulence, stomatitis.

Hemic and Lymphatic System: Ecchymosis.

Metabolic and Nutritional Disorders: Peripheral edema.

Musculoskeletal System: Leg cramps.

Nervous System: Abnormal dreams, confusion, paresthesia, speech disorder, thinking abnormalities.

Respiratory System: Dyspnea, sinusitis.

Skin and Appendages: Pruritus.

Urogenital System: Metrorrhagia.

Although the safety of ER and DR formulations were not assessed in the same study, a cross-study comparison of the data presented in Tables 11 and 12 suggest that the rate of adverse events were similar in the placebo-treated patients of the three well-controlled randomized studies. It is evident from Tables 11 and 12 that while the adverse events in the placebo-treated subjects were similar, Depakote ER-treated patients had lower number of adverse events compared to the Depakote DR-treated patients. It can be deduced that the reduced adverse events seen with Depakote ER treatment compared to Depakote DR treatment is probably due to the expected lower maximal plasma concentrations ($C_{max}$) and DFL that would be achieved, as illustrated in Examples 3 & 4, following administration of equal doses of two the formulations. It is reasonably believed that the reduced adverse effects, as well as lower frequency of dosing (once-a-day) dosing achieved with Depakote ER, would lead to better compliance.

The controlled release tablet formulations of the present invention thus provide an effective delivery system for the once daily administration of valproic acid (divalproex sodium) to patients in need of such treatment. The formulations of the invention provide substantially level plasma concentrations of valproic acid falling within the therapeutic range of the drug over a period which permits administration once daily. Further the incidence of side effects associated with valproate therapy has been reduced with this new formulation.

Example 6

Dissolution Method and Data

The following example illustrates the dissolution method of this application carried out on a tablet prepared as in Example 2.

Dissolution of tablet was tested using USP dissolution apparatus 2 operating at 37° C. with a paddle rotating speed of 100 rpm. The tablet was tested in 500 ml of 0.1N HCl for the first 45 minutes, followed by 900 ml of 0.05M phosphate buffer containing 75 mM SLS at pH 5.5. Samples were taken at 1, 3, 5, 9, 12 and 18 hours and assayed using TDx fluorescence polarization immunoassay (FPIA) technology. Dissolution data of commercial tablet:

| Time (hr) | 1.00 | 3.00 | 5.00 | 9.00 | 12.00 | 18.00 |
|---|---|---|---|---|---|---|
| % dissolved | 3.60 | 17.90 | 29.00 | 48.40 | 71.30 | 101.10 |

While there have been shown and described what are the preferred embodiments of the invention, one skilled in the pharmaceutical formulation art will appreciate that various modifications in the formulations and process can be made without departing from the scope of the invention as it is defined by the appended claims.

We claim:

1. An oral hydrophilic matrix formulation suitable for once-a-day administration comprising:

a) from about 40 to about 80 w/w % of divalproex sodium;

b) said divalproex sodium is in admixture with about 20 to about 50 w/w % of a pharmaceutically acceptable hydrophilic polymer selected from the group consisting of polyvinylpyrolidine, hydroxypropyl cellulose, hydroxypropylmethyl cellulose, methyl cellulose, vinyl acetate copolymers, polyethyleine oxide, methacrylic acid copolymers, and maleic anhydride/methyl vinyl ether copolymers, and;

c) said formulation exhibits the following in-vitro dissolution profile, when measured in a type 2 dissolution apparatus, paddle, at 100 rpm, at a temperature of 37+0.5 C., in 500 ml of 0.1N HCl for 45 minutes, followed by 900 ml of 0.05M phosphate buffer containing 75 mM sodium laurel sulfate, pH 5.5, for the remainder of the testing period:

i. no more than about 30% of total valproate is released after 3 hours of measurement in said apparatus;

ii. from about 40 to about 70% of total valproate is released after 9 hours of measurement in said apparatus;

iii. from about 55 to about 95% of total valproate is released after 12 hour of measurement in said apparatus, and;

iv. not less than 85% of total valproate is released after 18 hours of measurement in said apparatus.

2. The formulation according to claim 1 in which said formulation exhibits the following in-vitro dissolution profile:
   i. from about 15% to about 30% of total valproate is released after 3 hours of measurement in said apparatus;
   ii. from about 40% to about 70% of total valproate is released after 9 hours of measurement in said apparatus;
   iii. from about 55% to about 90% of total valproate is released after 12 hours of measurement in said apparatus, and;
   iv. not less than 88% of total valproate is released after 18 hours of measurement in said apparatus.

3. The formulation according to claim 1 in which said divalproex sodium is present in the amount of from about 45 to about 65 w/w %, based upon the total weight of the formulation.

4. The formulation according to claim 1 which further comprises one or more pharmaceutically acceptable excipients.

5. The formulation according to claim 1, which when ingested orally by healthy human subjects:
   a. produces a $C_{max}$ that is statistically significantly lower than the $C_{max}$ produced by a delayed release enteric coated divalproex sodium tablet given twice daily, when each is determined at steady state in a healthy fasting population;
   b. produces a $C_{min}$ that is not statistically significantly different from the $C_{min}$ produced by said delayed release divalproex sodium tablet, when each is determined at steady state in a healthy fasting population, and;
   c. said formulation produces an AUC value that is equivalent to the AUC value generated by said divalproex sodium delayed release tablet, when each is determined at steady state in a healthy fasting population.

6. An oral hydrophilic matrix formulation suitable for once-a-day administration comprising:
   a) from about 40 to about 80 w/w % of divalproex sodium;
   b) said divalproex sodium is in admixture with about 20 to about 50 w/w % of a pharmaceutically acceptable hydrophilic polymer selected from the group consisting of polyvinylpyrolidine, hydroxypropyl cellulose, hydroxypropylmethyl cellulose, methyl cellulose, vinyl acetate copolymers, polyethyleine oxide, methacrylic acid copolymers, and maleic anhydride/methyl vinyl ether copolymers, and
   c) said formulation exhibits the following in-vitro dissolution profile, when measured in a type 2 dissolution apparatus, paddle, at 100 rpm, at a temperature of 37+0.5 C., in 500 ml of 0.1N HCl for 45 minutes, followed by 900 ml of 0.05M phosphate buffer containing 75 mM sodium laurel sulfate, pH 5.5, for the remainder of the testing period:
      i. from about 15% to about 27% of total valproate is released after 3 hours of measurement in said apparatus;
      ii. from about 44% to about 69% of total valproate is released after 9 hours of measurement in said apparatus;
      iii. from about 59% to about 90% of total valproate is released after 12 hours of measurement in said apparatus, and;
      iv. not less than 88% of total valproate is released after 18 hours of measurement in said apparatus.

7. A method for the treatment of migraine comprising the administration of a formulation according to claim 1 to a patient in need thereof.

8. A method for the treatment of migraine comprising the administration of a formulation according to claim 6 to a patient in need thereof.

* * * * *